US009569838B2

(12) United States Patent
Enomoto

(10) Patent No.: US 9,569,838 B2
(45) Date of Patent: Feb. 14, 2017

(54) IMAGE PROCESSING APPARATUS, METHOD OF CONTROLLING IMAGE PROCESSING APPARATUS AND STORAGE MEDIUM

(75) Inventor: Makoto Enomoto, Kawasaki (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 14/114,823

(22) PCT Filed: May 31, 2012

(86) PCT No.: PCT/JP2012/064613
§ 371 (c)(1),
(2), (4) Date: Oct. 30, 2013

(87) PCT Pub. No.: WO2012/169562
PCT Pub. Date: Dec. 13, 2012

(65) Prior Publication Data
US 2014/0064563 A1 Mar. 6, 2014

(30) Foreign Application Priority Data
Jun. 9, 2011 (JP) ................................. 2011-129542

(51) Int. Cl.
*G06K 9/00* (2006.01)
*G06T 7/00* (2006.01)
*A61B 5/00* (2006.01)

(52) U.S. Cl.
CPC ........... *G06T 7/0012* (2013.01); *A61B 5/0013* (2013.01); *A61B 5/0077* (2013.01); *A61B 5/441* (2013.01);
(Continued)

(58) Field of Classification Search
CPC ..... A61B 5/0013; A61B 5/0033; A61B 5/441; A61B 5/447; A61B 5/748; G06T 2207/10024; G06T 2207/30088; G06T 2207/30096
(Continued)

(56) References Cited

U.S. PATENT DOCUMENTS

| 7,412,081 B2* | 8/2008 | Doi | ................. G06F 21/32 382/115 |
|---|---|---|---|
| 2003/0085908 A1 | 5/2003 | Luby | ............................ 345/619 |
| 2010/0138757 A1* | 6/2010 | Shigenobu | ......... H04N 1/00411 715/760 |

FOREIGN PATENT DOCUMENTS

| JP | A 05-180699 | 7/1993 |
|---|---|---|
| JP | A 2006-141581 | 6/2006 |

(Continued)

OTHER PUBLICATIONS

B. McGregor, "Automatic Registration of Images of Pigmented Skin Lesions", *Pattern Recognition*, vol. 31, No. 6, pp. 805-817 XP004118873 (Jun. 1998).
D. A. Perednia et al., "Automatic Registration of Multiple Skin Lesions by Use of Point Pattern Matching", *Computerized Medical Imaging and Graphics*, vol. 16, No. 3, pp. 205-216 XP002916209 (May-Jun. 1992).
M. M. Rahman et al., "Image Retrieval-Based Decision Support System for Dermatoscopic Images", *19th IEEE International Symposium on Computer-Based Medical Systems*, 2006, Salt Lake City, UT, USA Jun. 22-23, 2006, Piscataway, NJ USA, IEEE, XXP031668653 (6 pages; no page numbers; no publ. date apart from date of conference).

(Continued)

*Primary Examiner* — Amara Abdi
(74) *Attorney, Agent, or Firm* — Fitzpatrick, Cella, Harper & Scinto

(57) ABSTRACT

An image processing apparatus comprises: detection means for detecting a region corresponding to a diseased part reference region other than a diseased part region in an input image; and identifying means for identifying the diseased part region based on the corresponding region detected by the detection means.

9 Claims, 10 Drawing Sheets

(52) U.S. Cl.
CPC ............. *A61B 5/447* (2013.01); *A61B 5/6898* (2013.01); *A61B 5/748* (2013.01); *A61B 5/7425* (2013.01); *G06T 7/0016* (2013.01); *G06T 2207/10024* (2013.01); *G06T 2207/30088* (2013.01); *G06T 2207/30096* (2013.01)

(58) Field of Classification Search
USPC ......................................................... 382/103
See application file for complete search history.

(56) References Cited

FOREIGN PATENT DOCUMENTS

| | | | | |
|---|---|---|---|---|
| JP | A 2010-177774 | | 8/2010 | |
| JP | A 2010-187711 | | 9/2010 | |
| WO | WO 2006/078902 | * | 7/2006 | ............... G06T 7/00 |
| WO | WO2006/078902 | * | 7/2006 | ............... G06T 7/00 |

OTHER PUBLICATIONS

P. Viola et al., "Rapid Object Detection using a Boosted Cascade of Simple Features", IEEE Computer Society Conference on Computer Vision and Pattern Recognition, 2001, vol. 1, pp. I-511 through I-518 (2001).
R. G. White et al., "Automatic Derivation of Initial Match Points for Paired Digital Images of Skin", *Computerized Medical Imaging and Graphics*, vol. 16, No. 3, pp. 217-225, XP022916210 (May-Jun. 1992).
Office Action issued Jul. 31, 2015 in counterpart Japanese patent application 2011-129542, with partial translation.

* cited by examiner

| IMAGE SIZE | 3000 HORIZONTAL | 4000 VERTICAL |
|---|---|---|
| DISEASED PART REGION | CENTER (1500,1600) | DIAMETER (400,600) |

| IMAGE SIZE | 3000 HORIZONTAL | 4000 VERTICAL |
|---|---|---|
| DISEASED PART REGION | CENTER (1500,1600) | DIAMETER (400,600) |
| OUTER DIAMETER OF DISEASED PART REFERENCE REGION | CENTER (1500,1600) | DIAMETER (800,1200) |
| INNER DIAMETER OF DISEASED PART REFERENCE REGION | CENTER (1500,1600) | DIAMETER (400,600) |

IMAGE PROCESSING APPARATUS, METHOD OF CONTROLLING IMAGE PROCESSING APPARATUS AND STORAGE MEDIUM

TECHNICAL FIELD

The present invention relates to an image processing apparatus, a method of controlling the image processing apparatus, a storage medium and, more particularly, to an image processing apparatus which performs recognition processing on medical images, a method of controlling the image processing apparatus, and a storage medium.

BACKGROUND ART

With recent advances in computerization in medical organizations such as hospitals, an increasing number of organizations have introduced electronic medical charts which manage patient diagnosis information. Each electronic medical chart unitarily manages, on it, the diagnosis history, medication information, surgical information, diseased part images, X-ray images, and the like of each patient, and allows to easily share and reuse data. Recent increases in storage capacity have allowed electronic medical charts to store large quantities of digital images of diseased parts and the like upon image-sensing them.

In such an environment, a technique for storing, in electronic medical charts, images obtained by image-sensing patients using digital cameras as medical records, is frequently used. In a dermatology department, surgery department, and nursing field, the images of wounds, operative scars, and pressure ulcers (bedsores) of patients are periodically sensed by digital cameras to observe temporal changes in the diseased parts.

Recent advances in communication technology have been implementing remote medical care at home. An increasing number of patients themselves now take pictures of diseased parts using image sensing apparatuses such as general-purpose digital cameras, transmit the pictures to medical organizations, and receive diagnoses from doctors. In such a state in which patients themselves perform image sensing, it is difficult, depending on the region of a patient, to capture the proper diseased part image while seeing an output image from an image sensing apparatus.

As a method of solving the problem of difficulty in image-sensing diseased parts, there is conceivable a method of automatically detecting a specific region at the time of image sensing by learning the region. As a detection method, there is available, for example, "Rapid Object Detection Using a Boosted Cascade of Simple Features", Viola, P. and Jones, M., IEEE COMPUTER SOCIETY CONFERENCE ON COMPUTER VISION AND PATTERN RECOGNITION, 2001, VOL 1, pages I-511-I-518. This method acquires a feature amount from a teacher image in advance, obtains the feature amounts of all partial images in an input image, and compares the feature amounts with each other to determine whether each partial image is similar to the teacher image.

An image processing method disclosed in Japanese Patent Laid-Open No. 05-180699 detects a diseased part region by using a special marker when it is difficult to detect the diseased part position by surface temperature image sensing.

The method of detecting by learning a diseased part region has a problem that it is difficult to detect temporal changes including improvements and deteriorations in the symptom of a diseased part. In addition, learning from many teacher data including the follow-up of symptoms in a general purpose manner will increase the variance of features, resulting in a deterioration in detection accuracy.

SUMMARY OF INVENTION

In consideration of the above problems, the present invention provides a technique of detecting a diseased part without being influenced by a change in the diseased part with the lapse of time.

According to one aspect of the present invention, there is provided an image processing apparatus comprising: detection means for detecting a region corresponding to a diseased part reference region other than a diseased part region in an input image; and identifying means for identifying the diseased part region based on the corresponding region detected by the detection means.

According to one aspect of the present invention, there is provided a method of controlling an image processing apparatus, comprising: a detection step of detecting a region corresponding to a diseased part reference region other than a diseased part region in an input image; and an identifying step of identifying the diseased part region based on the corresponding region detected in the detection step.

Further features of the present invention will be apparent from the following description of exemplary embodiments with reference to the attached drawings.

DESCRIPTION OF EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 1:
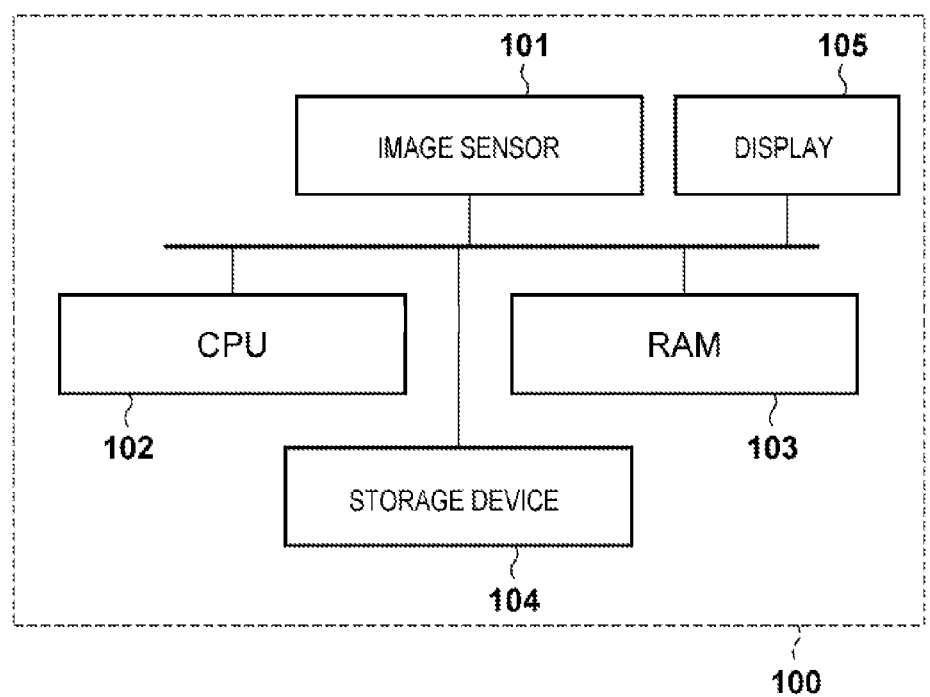
FIG. 1 is a block diagram showing an example of the arrangement of an image processing apparatus according to the present invention.

FIG. 1 shows an example of the arrangement of an image processing apparatus which carries out the present invention. An image processing apparatus 100 includes an image sensor 101, a CPU 102, a RAM 103, a storage device 104, and a display 105. The display 105 may be an external device and need not always be incorporated in the image processing apparatus 100.

The image sensor 101 converts an image passing through an optical system such as a lens into electronic image information.

The CPU 102 controls the respective constituent elements by executing an image processing program for the execution of processing according to the present invention for image information input from the image sensor 101. The RAM 103 is used as a work memory for the execution of an image processing program or used to temporarily store data.

The storage device 104 stores the image processing program and data.

The display 105 displays a through image as image information obtained from the image sensor 101, and displays an image stored in the storage device 104. In this case, a through image is an image acquired from an image sensor at predetermined intervals to determine a composition at the time of image sensing.

The arrangement of the image processing apparatus 100 is an example, and it is possible to use a portable device such as a cellular phone or PDA which has an image sensor. It is also possible to execute image processing by using an external general-purpose computer. Assume that in this embodiment, a digital camera includes all components.

Figure 2:
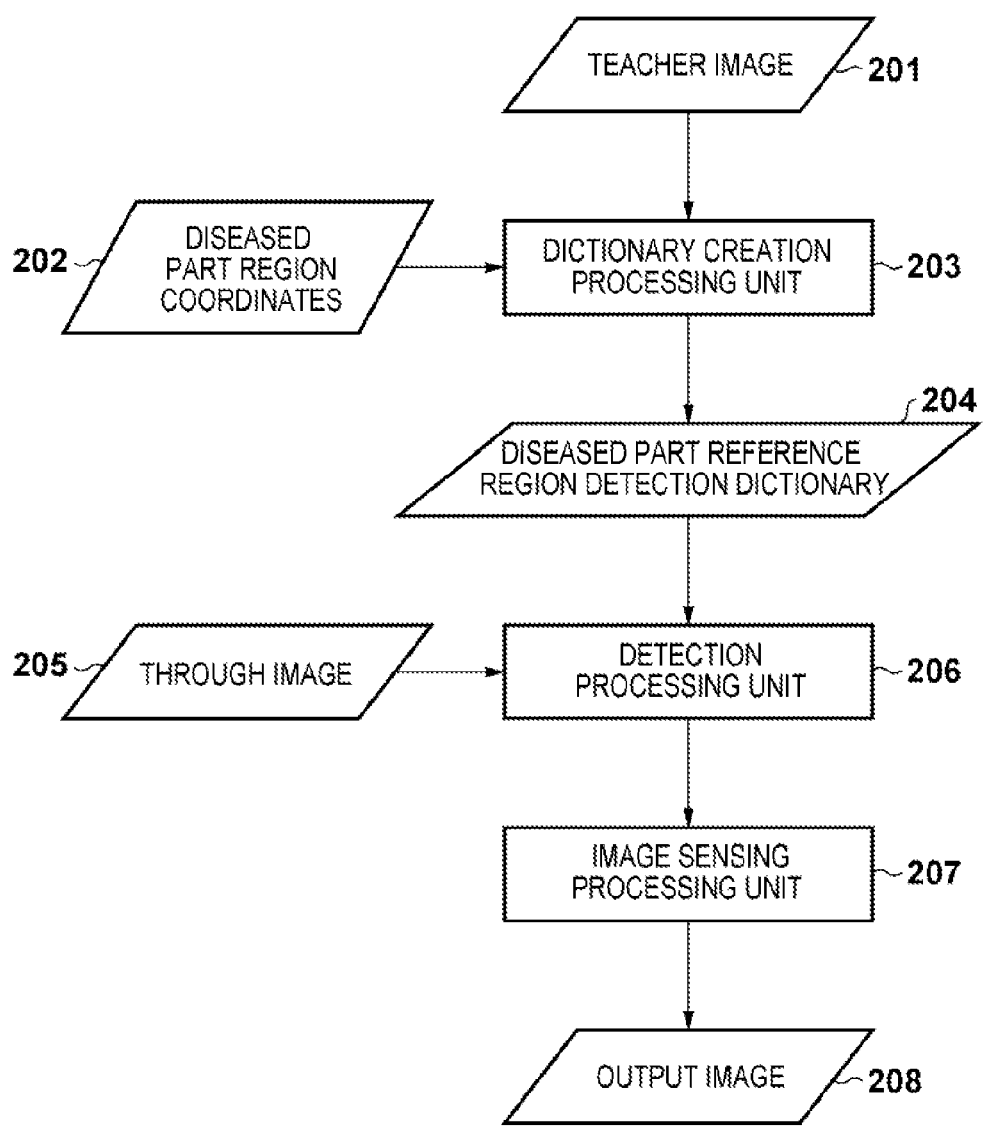
FIG. 2 is a functional block diagram of the image processing apparatus according to the present invention.

FIG. 2 is a functional block diagram of the image processing apparatus according to the present invention. Teacher image data 201 is data for the creation of a detection dictionary (dictionary data). The teacher image data 201 needs to include at least a diseased part region as a detection target.

Diseased part region coordinate data 202 is data representing a diseased part region corresponding to the teacher image data 201.

A dictionary creation processing unit 203 acquires the teacher image data 201 and the diseased part region coordinate data 202 and creates a diseased part reference region detection dictionary 204 for the detection of a diseased part reference region. A diseased part reference region is a region, other than a diseased part, which allows to obtain the coordinates of a diseased part and exhibits a slight change with the lapse of time. A region which exhibits a slight change with the lapse of time is a region which undergoes a small change with the lapse of time relative to a diseased part which exhibits a large change in color or contour due to an improvement or deterioration of symptoms. Such a region includes the skin of a portion around the diseased part. This embodiment uses a portion around a diseased part, that is, a region having a doughnut shape which immediately surrounds a diseased part. In this case, if an image region includes all the doughnut shape around a diseased part, it can be said that the diseased part region also exists in the image.

The diseased part reference region detection dictionary 204 is a dictionary for detecting a diseased part reference region created by the dictionary creation processing unit 203.

A through image 205 is an image acquired from the image sensor 101 at predetermined intervals to determine a composition at the time of image sensing. A diseased part reference region is detected by using the through image 205.

A detection processing unit 206 determines, by using the diseased part reference region detection dictionary 204 and the through image 205, whether an image includes a diseased part reference region.

An image sensing processing unit 207 actually performs image sensing based on the detection result obtained by the detection processing unit 206. If the through image 205 includes an entire diseased part reference region, since the through image includes the diseased part region, the image sensing processing unit 207 performs image sensing upon setting image sensing conditions.

An output image 208 is an image obtained by image sensing performed by the image sensing processing unit 207. This operation obtains a photographic image including an entire diseased part reference region, that is, a diseased part region, within the field angle.

Figure 3:
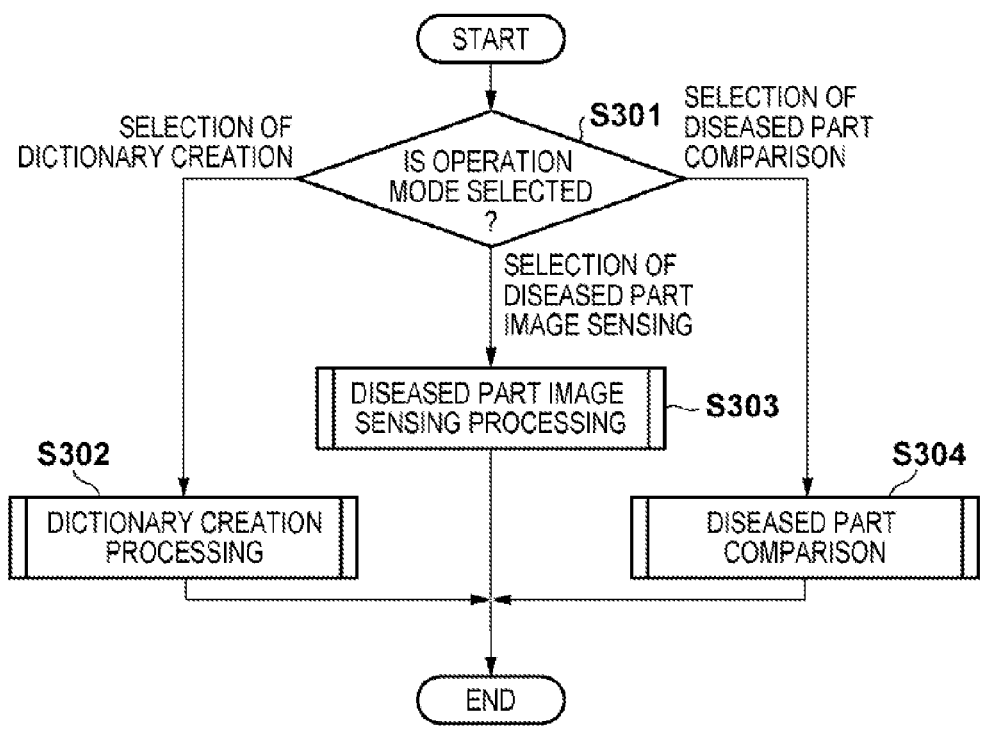
FIG. 3 is a flowchart showing a procedure for processing according to the first embodiment.

A procedure for processing according to this embodiment will be described next with reference to the flowchart of FIG. 3.

In step S301, the dictionary creation processing unit 203 accepts selection by operation of the user. In this embodiment, the dictionary creation processing unit 203 accepts the selection of one of the following modes: a dictionary creation mode for creating the diseased part reference region detection dictionary 204, a diseased part image sensing selection mode for obtaining the output image 208 by detecting and image-sensing the diseased part, and a diseased part comparison mode for reproducing the output image 208. If the dictionary creation mode is selected, the process advances to step S302. If the diseased part image sensing mode is selected, the process advances to step S303. If the diseased part comparison mode is selected, the process advances to step S304.

In step S302, the dictionary creation processing unit 203 performs dictionary creation processing. Dictionary creation processing will be described in detail later with reference to the flowchart shown in FIG. 7.

In step S303, the detection processing unit 206 and the image sensing processing unit 207 perform the processing of identifying and image-sensing a diseased part region. This processing will be described in detail later with reference to the flowchart shown in FIG. 8.

In step S304, the display 105 comparatively displays the diseased part by simultaneously displaying a plurality of diseased part images. This display operation will be described in detail later with reference to FIGS. 10A and 10B. Thereafter, the processing is terminated.

Figure 7:
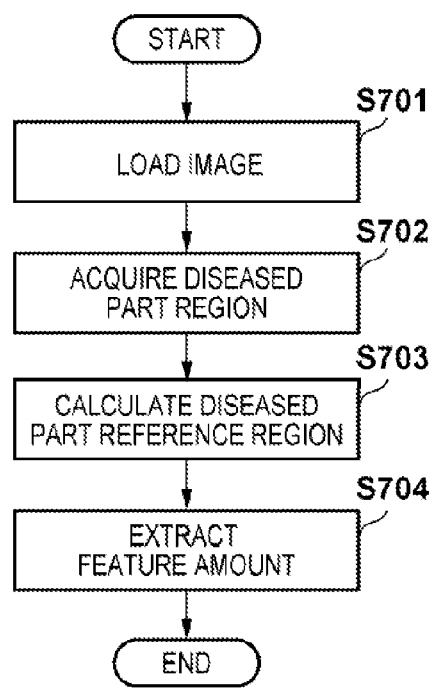
FIG. 7 is a flowchart showing a processing procedure in a dictionary creation processing unit in the first embodiment.

A procedure for dictionary creation processing (step S302) will be described in detail below with reference to the flowchart of FIG. 7.

Figure 4:
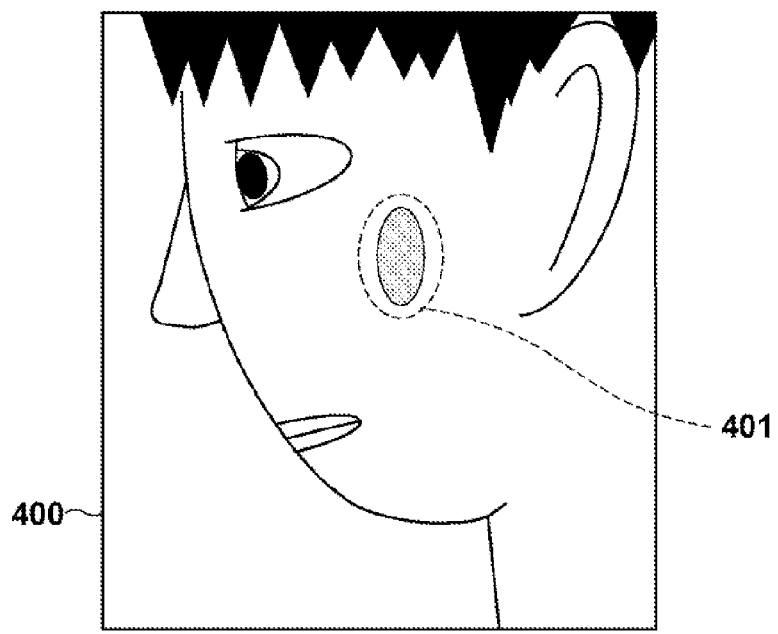
FIG. 4 is a view showing an example of a teacher image in the first embodiment.

In step S701, the CPU 102 loads a teacher image 400 like that shown in FIG. 4 in the RAM 103 as an example of the teacher image data 201 used for dictionary creation processing described with reference to FIG. 2. Referring to FIG. 4, the teacher image 400 is an image obtained by image-sensing the head portion of a patient from a side face. The region enclosed by the broken line is a diseased part 401 included in the teacher image 400. The teacher image 400 may be externally supplied in the form of image data or may be acquired by using the image sensor 101.

Figures 5A, 5B:
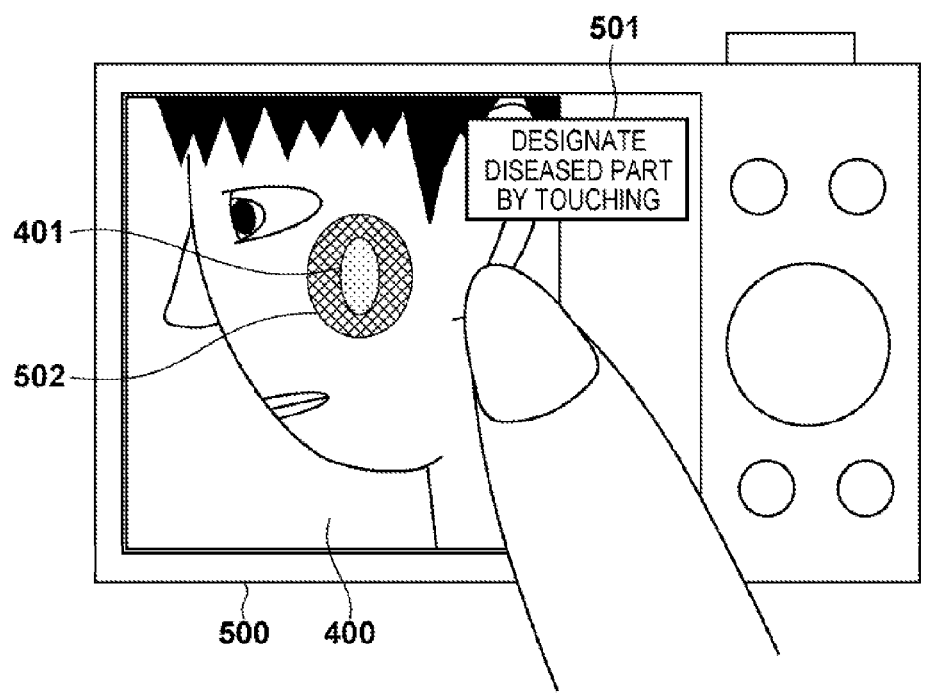
FIGS. 5A and 5B are views each showing an example of a diseased part region in the first embodiment.

In step S702, the CPU 102 acquires a diseased part region from the teacher image 400. FIG. 5A shows an example of a user interface (UI) which accepts the designation of a diseased part region. A touch panel display 501 on a digital camera 500 displays the teacher image 400 acquired in step S701. The user selects a diseased part region 502 by tracing the boundary of the diseased part 401 on the touch panel display 501 with his/her finger (designation acceptance processing). Assume that coordinate data like those shown in FIG. 5B are obtained as an example of the diseased part region coordinates 202 described with reference to FIG. 2 with respect to the diseased part region 502 selected by this operation. The image size is 3000 pixels horizontal×4000 pixels vertical. Assume that the CPU 102 has obtained an elliptic region defined such that the central coordinates of the diseased part region 502 are (1500 pixels, 1600 pixels), and the diameter is (400 pixels, 600 pixels). Although this embodiment has exemplarily used an elliptic shape for the sake of descriptive convenience, it is possible to use a rectangular shape or a shape represented by a region enclosed by a free curve represented by Bezier coordinates.

Figures 6A, 6B:
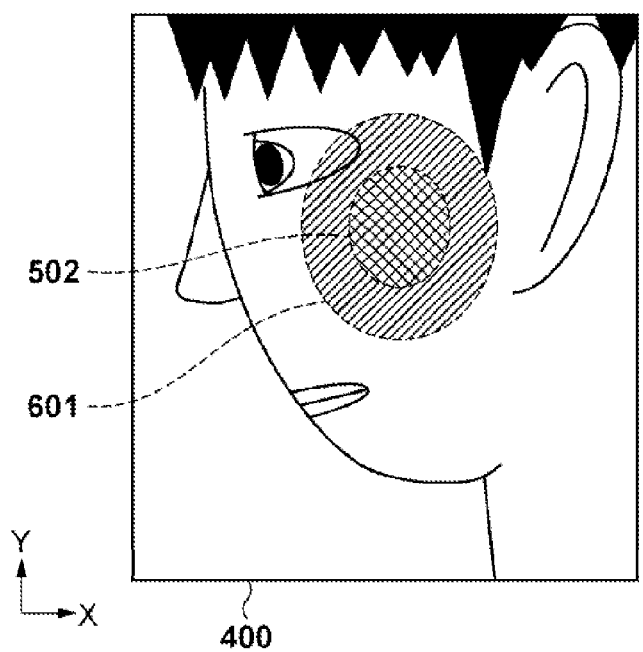
FIGS. 6A and 6B are views each showing an example of a diseased part reference region acquisition result in the first embodiment.

In step S703, the CPU 102 calculates a diseased part reference region. In this case, the CPU 102 calculates a region around the diseased part region 502 shown in FIG. 6A as a diseased part reference region 601. That is, the CPU 102 calculates the diseased part reference region 601 in an elliptic annular shape by simply doubling the diameter of the diseased part region 502 in the form of a concentric ellipse and subtracting the diseased part region 502 from the resultant region. Although the diseased part reference region 601 is simply a predetermined region (elliptic annular region) around the diseased part region, a feature point such as the eye or ear may be a diseased part reference region when handling, for example, a face. Assume that the CPU 102 has obtained an elliptic annular region represented by the coordinate data shown in FIG. 6B as the coordinate data of the diseased part reference region 601. The image size is 3000 pixels horizontal×4000 pixels vertical. The central coordinates of the diseased part region 502 are (1500 pixels, 1600 pixels), and the diameter is (400 pixels, 600 pixels). Likewise, the central coordinates of the outer diameter of the diseased part reference region 601 are (1500 pixels, 1600 pixels), and the diameter is (800 pixels, 1200 pixels). The central coordinates of the inner diameter of the diseased part reference region 601 are (1500 pixels, 1600 pixels), and the diameter is (400 pixels, 600 pixels).

In step S704, the CPU 102 controls the dictionary creation processing unit 203 to create the diseased part reference region detection dictionary 204 by extracting a feature amount such as a color or line segment from the diseased part reference region 601 obtained in step S703. As a known method of extracting a feature amount and performing detection using it, there is available "Rapid Object Detection Using a Boosted Cascade of Simple Features", Viola, P. and Jones, M., IEEE COMPUTER SOCIETY CONFERENCE ON COMPUTER VISION AND PATTERN RECOGNITION, 2001, VOL 1, pages I-511-I-518. According to "Rapid Object Detection Using a Boosted Cascade of Simple Features", Viola, P. and Jones, M., IEEE COMPUTER SOCIETY CONFERENCE ON COMPUTER VISION AND PATTERN RECOGNITION, 2001, VOL 1, pages I-511-I-518, there is disclosed a technique of acquiring a feature amount from a teacher image, obtaining feature amounts associated with all partial images in an input image, and obtaining a region similar to the teacher image from the input image by discriminating whether each feature amount obtained is similar to that of the teacher image. In the present invention, a target to be detected is a region unique to a specific patient, that is, the variance of feature amounts is limited, and hence it is not necessary to use many teacher images as described in "Rapid Object Detection Using a Boosted Cascade of Simple Features", Viola, P. and Jones, M., IEEE COMPUTER SOCIETY CONFERENCE ON COMPUTER VISION AND PATTERN RECOGNITION, 2001, VOL 1, pages I-511-I-518. Alternatively, it is possible to simply hold an image of the diseased part reference region 602 as data in a dictionary and perform detection by using a technique such as a similar image search technique.

Figure 8:
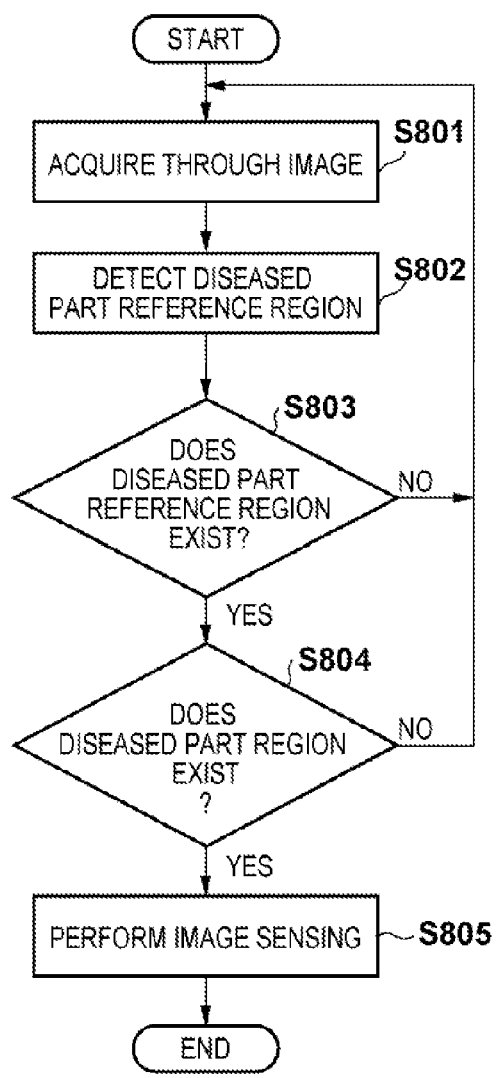
FIG. 8 is a flowchart showing a procedure for diseased part image sensing processing in the first embodiment.
Figure 9A:
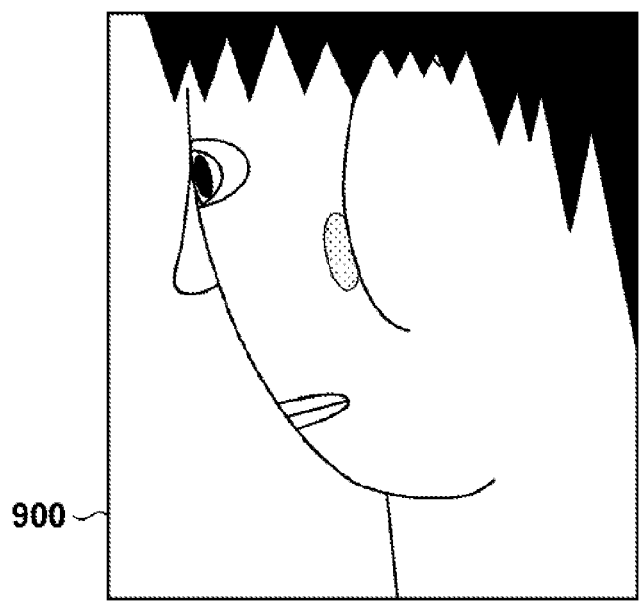
FIGS. 9A and 9B are views each showing an example of a detection processing result in the first embodiment.
Figure 9B:
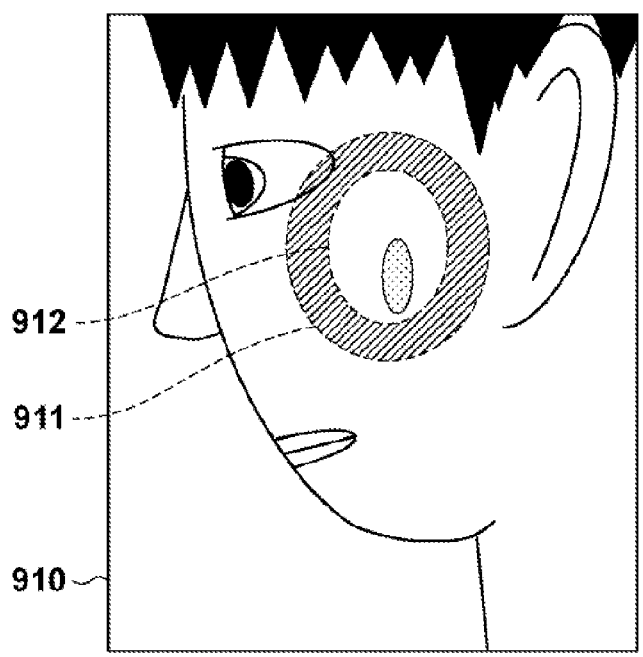

Diseased part image sensing processing (step S303) will be described in detail next with reference to the flowchart of FIG. 8 in a case in which a through image 900 shown in FIG. 9A and a through image 910 shown in FIG. 9B are sequentially input, each as an example of the through image 205. In this case, the through image 900 is an image obtained when the object is observed from obliquely behind, and the through image 910 is an image obtained when the object is observed from a side face.

In step S801, the CPU 102 controls the detection processing unit 206 to acquire the through image 205 from the image sensor (image sensor 101). Assume that in this case, the process advances to step S802 on the assumption that the through image 900 has been newly obtained as the through image 205.

In step S802, the CPU 102 controls the detection processing unit 206 to detect a region corresponding to the diseased part reference region 601 which is registered in the diseased part reference region detection dictionary 204 from the through image 900 by using the diseased part reference region detection dictionary 204. As described in the feature amount extraction processing in step S704, the CPU 102 detects a region with an approximate feature based on features such as colors and shapes registered as data in a dictionary. As a known method for this operation, there is available "Rapid Object Detection Using a Boosted Cascade of Simple Features", Viola, P. and Jones, M., IEEE COMPUTER SOCIETY CONFERENCE ON COMPUTER VISION AND PATTERN RECOGNITION, 2001, VOL 1, pages I-511-I-518. In the case of the through image 900, since the composition of the image greatly differs from that of the teacher image 400, the process advances to step S803 upon determining that no region corresponding to the diseased part reference region 601 has been detected.

In step S803, the CPU 102 controls the detection processing unit 206 to discriminate whether a region corresponding to the diseased part reference region 601 has been detected in step S802. If the detection processing unit 206 discriminates that a region corresponding to the diseased part reference region 601 has been detected (YES in step S803), the process advances to step S804. In contrast, if the detection processing unit 206 discriminates that no region corresponding to the diseased part reference region 601 has been detected (NO in step S803), the process returns to step S801. In this case, since no region corresponding to the diseased part reference region 601 has been detected, the process returns to step S801.

In step S801, the CPU 102 controls the detection processing unit 206 to acquire the through image 205 from the image sensor (image sensor 101). In this case, the process advances to step S802 on the assumption that the through image 910 has been obtained as the through image 205.

In step S802, the CPU 102 controls the detection processing unit 206 to discriminate from the through image 910 that the feature of a detected region 911 indicated by the hatching in an elliptic annular shape coincides with that of the diseased part reference region 601. The process then advances to step S803.

In step S803, the CPU 102 controls the detection processing unit 206 to discriminate whether a region corresponding to the diseased part reference region 601 has been detected in step S802. In this case, since a region corresponding to the diseased part reference region 601 has been detected, the process advances to step S804.

In step S804, the CPU 102 controls the detection processing unit 206 to determine from the detected position information of the region corresponding to the diseased part reference region 601 whether the through image 910 includes the diseased part region 502. If the detection processing unit 206 determines that the through image 910 includes the diseased part region 502 (YES in step S804), the process advances to step S805. If the detection processing unit 206 determines that the through image 910 does not include the diseased part region 502 (NO in step S804), the process returns to step S801. In this embodiment, since an elliptic portion having the same outer shape as the inner-diameter portion of the elliptic annular diseased part reference region 601 is the diseased part region 502, if the entire region corresponding to the diseased part reference region 601 falls within the through image 910, it is possible to determine that the through image includes the diseased part region. In this case, since the through image 910 includes the entire detected region 911, the CPU 102 determines that the diseased part is also included. The process then advances to step S805.

In step S805, the CPU 102 controls the image sensor 101 to actually perform image sensing. When performing image sensing processing by using a general digital camera, the CPU 102 adjusts parameters such as sensor sensitivity, exposure time, and white balance by using color histogram information, luminance histogram information, and the like of an image. The CPU 102 writes the through image 910 having a composition similar to that of the through image 910 in the storage device 104, and terminates the processing.

Figure 10A:
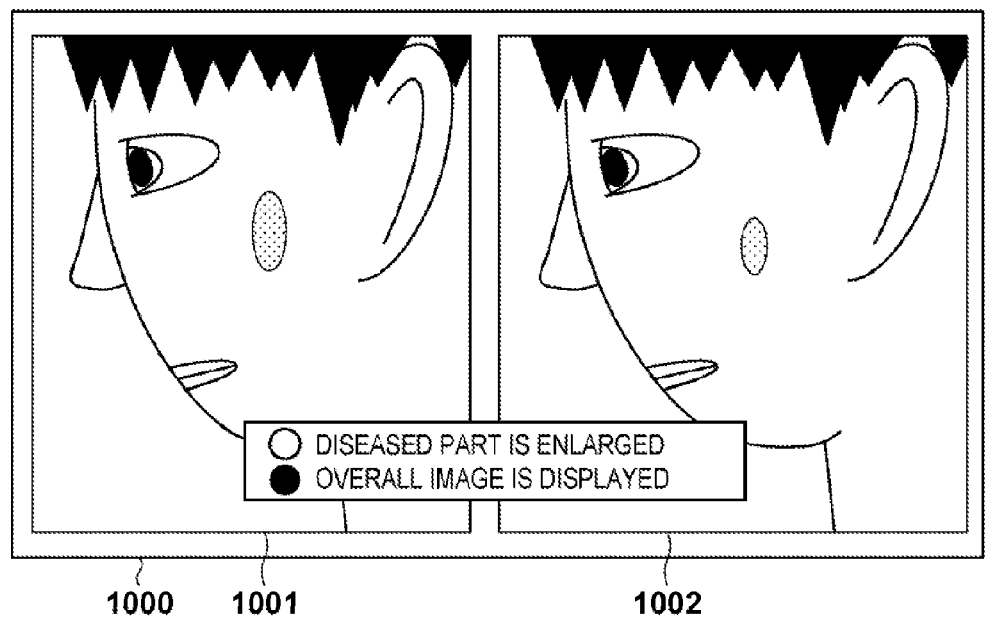
FIGS. 10A and 10B are views each showing an example of output image comparison in the first embodiment.
Figure 10B:
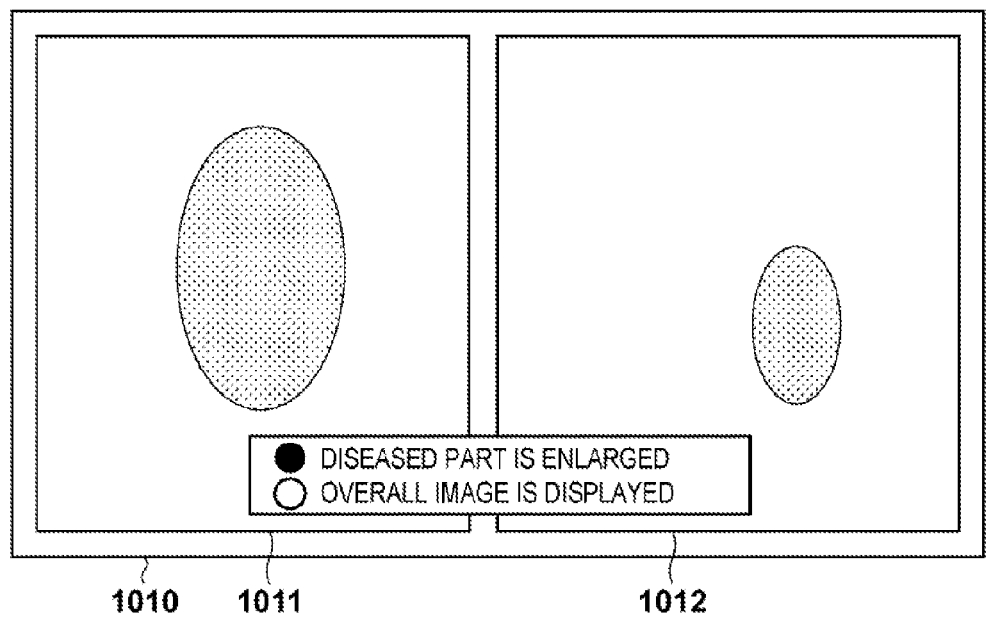

Diseased part comparison processing (step S304) will be described with reference to the display example shown in FIGS. 10A and 10B. FIGS. 10A and 10B each show an example of comparatively showing the teacher image 400 and an output image on the display 105. Referring to FIG. 10A, an overall display area 1000 displays the overall teacher image 400 in a display area 1001, and the overall output image 910 in a display area 1002. On the other hand, referring to FIG. 10B, an overall display area 1010 respectively displays, in a display area 1011 and a display area 1012, the images obtained by enlarging the teacher image 400 and the output image 910, based on the diseased part region 502 obtained in step S702 and a diseased part region 912 obtained in step S804, so as to make the two regions have the same size. Displaying these regions upon matching the sizes of the diseased parts allows to check for changes in the diseased part over a lapse of time more accurately.

As described above, according to this embodiment, creating a diseased part reference region detection dictionary in advance allows a patient himself/herself to easily image-sense a diseased part in a region which generally makes image sensing difficult and to observe a change in the symptom of the diseased part.

Second Embodiment

The first embodiment is configured to perform image sensing upon simply determining whether a diseased part region exists in a through image, that is, the field angle of the lens. Furthermore, in the second embodiment, adding a guidance for the user to approximate the composition of a through image to that of a teacher image can further facilitate self image sensing of a diseased part and difference comparison. Assume that a diseased part reference region detection dictionary 204 includes the position information and size information of a diseased part region in a teacher image.

Figure 11:
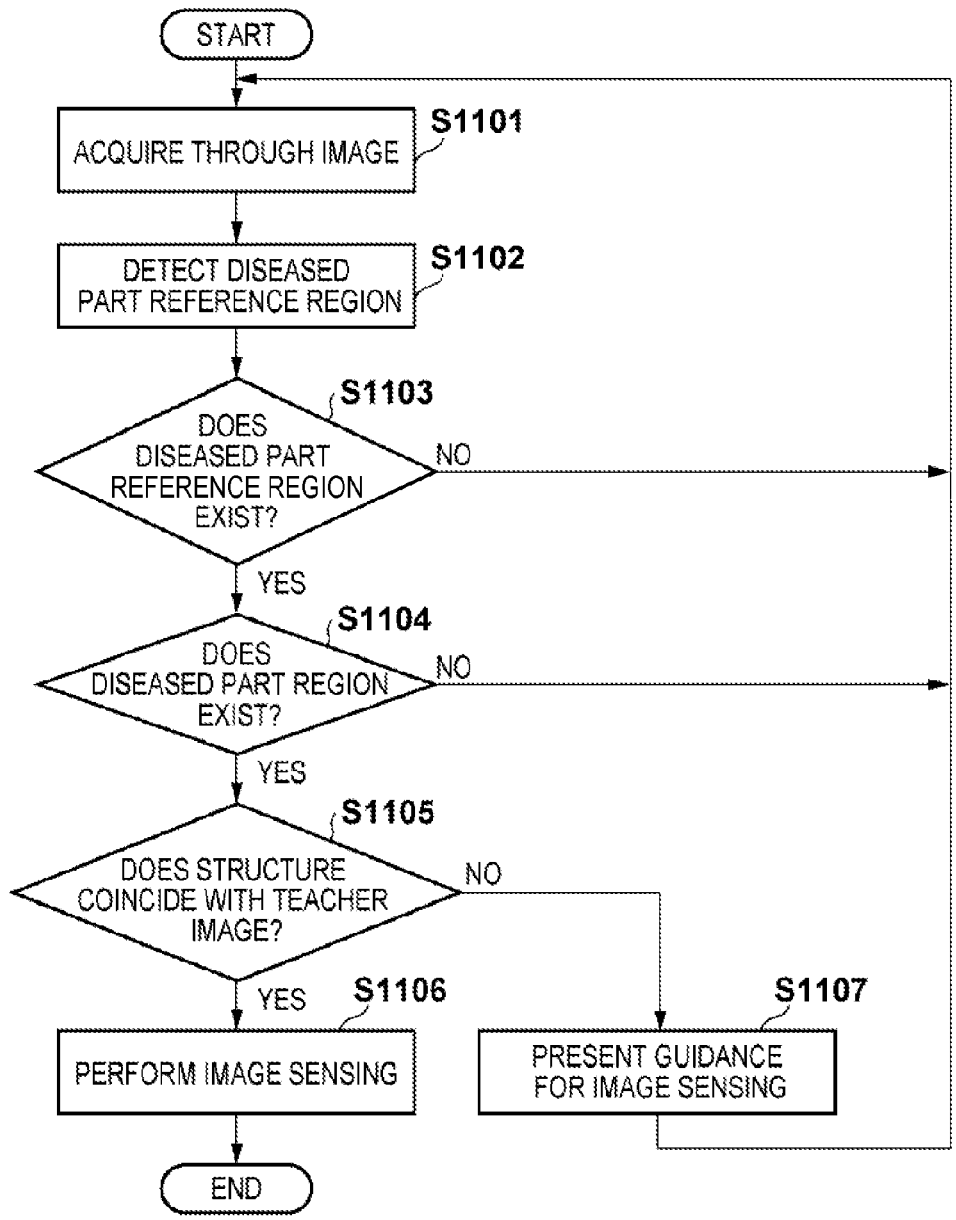
FIG. 11 is a flowchart showing a procedure for diseased part image sensing processing in the second embodiment.

A procedure for diseased part image sensing processing (step S303) according to this embodiment will be described with reference to the flowchart of FIG. 11.

Figure 12A:
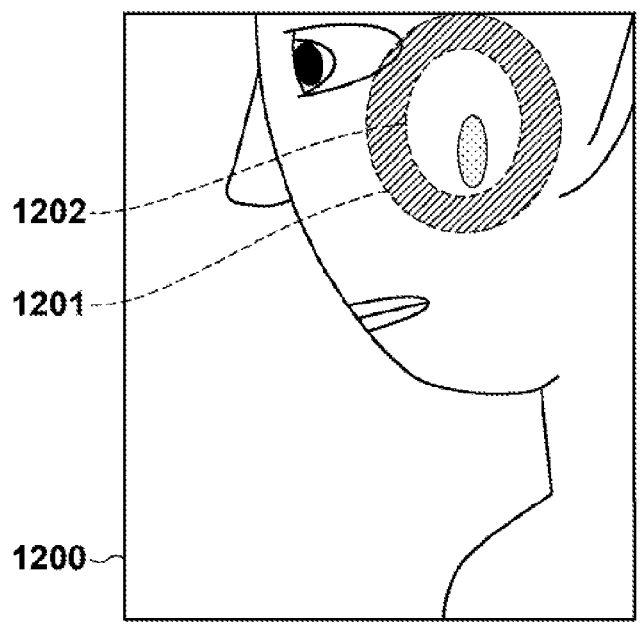
FIGS. 12A and 12B are views each showing an example of a detection processing result in the second embodiment.
Figure 12B:
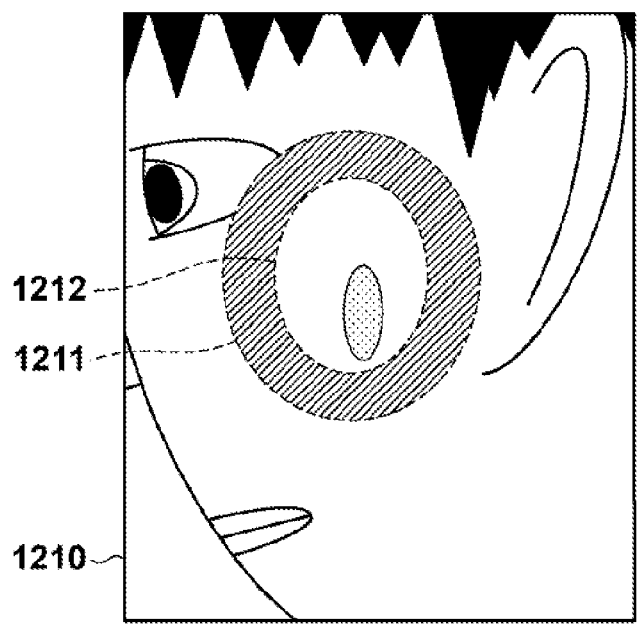

The following is the processing to be performed when a through image 1200 shown in FIG. 12A, a through image 1210 shown in FIG. 12B, and a through image 910 shown in FIG. 9B are sequentially input, each as an example of a through image 205.

In step S1101, a CPU 102 controls a detection processing unit 206 to acquire the through image 1200 from an image sensor (image sensor 101). In step S1102, the CPU 102 controls the detection processing unit 206 to detect, by using the diseased part reference region detection dictionary 204 created from a diseased part reference region 601, a similar region from the through image 1200. In the case of the through image 1200, since the detection processing unit 206 detects a region corresponding to a diseased part reference region 1201, the process advances to step S1103.

In step S1103, the CPU 102 controls the detection processing unit 206 to discriminate whether a region corresponding to the diseased part reference region 601 has been detected in step S1102. In this case, since a region corresponding to the diseased part reference region has been detected, the process advances to step S1104.

In step S1104, the CPU 102 controls the detection processing unit 206 to determine, from the detected position information of the diseased part reference region, whether the through image 1200 includes a diseased part region. If the detection processing unit 206 determines that the through image 1200 includes a diseased part region (YES in step S1104), the process advances to step S1105. If the detection processing unit 206 determines that the through image 1200 includes no diseased part region (NO in step S1104), the process returns to step S1101. In this case, since the through image 1200 includes the overall detected region 1201, the CPU 102 determines that the through image also includes the diseased part. The process then advances to step S1105.

In step S1105, the CPU 102 determines whether the image-sensed composition is similar to the teacher image. In this embodiment, the CPU 102 determines, depending on the position and size of the diseased part region in the image, whether the composition is similar to the teacher image. For example, the CPU 102 may determine, based on the position and size of a diseased part region, whether the composition is similar to the teacher image, depending on whether the area of an overlapping area is equal to or more than a threshold. If the CPU 102 determines that the image-sensed composition is similar to the teacher image (YES in step S1105), the process advances to step S1106. If the detection processing unit 206 determines that the image-sensed composition is not similar to the teacher image (NO in step S1105), the process advances to step S1107. A diseased part region 1202 calculated from the diseased part reference region 1201 is offset to the upper right on the image relative to an original teacher image 400, and hence the detection processing unit 206 determines that the image-sensed composition is not similar to the teacher image. The process then advances to step S1107. Note that the determination method in this embodiment is merely an example, and it is possible to use, as parameters, for example, an offset relative to the rotating direction, the tilts of a diseased part surface and lens surface, that is, distortion, and the like.

In step S1107, the CPU 102 presents an image sensing guidance to the user. Assume that this embodiment is configured to notify the user of an image sensing position by speech. Note that an image sensing guidance may be notified by displaying a message on a display 105. After the CPU 102 issues an instruction to move the image sensor 101 to the upper right by speech, the process returns to step S1101.

Likewise, assume that in step S1101, the CPU 102 has acquired the through image 1210 as the through image 205.

In step S1102, the CPU 102 detects a region corresponding to a diseased part reference region 1211. In step S1103, the CPU 102 determines that the diseased part reference region 1211 exists. In step S1104, the CPU 102 determines that a diseased part region 1212 exists. The process then advances to step S1105.

In step S1105, the CPU 102 determines whether the image-sensed composition is similar to the teacher image. In this case, since the diseased part region 1212 is larger than that in the teacher image, the process advances to step S1107.

In step S1107, the CPU 102 issues an instruction, by speech, to increase the distance between the image sensor 101 and the diseased part or shift the zoom lens to the wide angle side. The process then returns to step S1101.

Assume that in step S1101, the CPU 102 has acquired the through image 910 as the through image 205. Likewise, assume that the CPU 102 has detected a region corresponding to a diseased part reference region 911 in step S1102, determines in step S1103 that the diseased part reference region 911 exists, and determines in step S1104 that a diseased part region 912 exists. In this case, the process advances to step S1105.

In step S1105, the CPU 102 determines whether the image-sensed composition is similar to the teacher image. The CPU 102 determines, as a result of the comparison between the diseased part region 912 and the teacher image, that the similarity falls within a predetermined threshold range. The process then advances to step S1106.

In step S1106, the CPU 102 controls the image sensor 101 to acquire an output image having the same image-sensed composition as that of the through image 910 by image sensing processing. The CPU 102 then terminates the processing.

As described above, adding a guidance function for the user to the first embodiment can facilitate self image sensing operation and obtain a composition similar to a teacher image. This makes it possible to compare diseased parts with each other with high accuracy.

As has been described above, according to the present invention, it is possible to implement detection processing robust against a change in diseased part over the lapse of time by learning a region, other than a diseased part, such as a portion around the diseased part, which can identify the position of the diseased part.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-129542 filed on Jun. 9, 2011, which is hereby incorporated by reference herein in its entirety.

The invention claimed is:

1. An image processing apparatus comprising:
   a CPU and memory, programmed to operate as:
      a designation acceptance unit configured to accept designation of a first diseased part region from a first image of an object to be examined by a medical doctor;
      a determination unit configured to determine a first diseased part reference region, of the object to be examined by a medical doctor, surrounding the diseased part region accepted by said designation acceptance unit;
      a feature amount extraction unit configured to extract a feature amount in the diseased part reference region, of the object to be examined by a medical doctor, determined by said determination unit;
      a registration unit configured to register the feature amount in the diseased part reference region extracted by said feature amount extraction unit into dictionary data;
      a detection unit configured to detect from a second image a corresponding region corresponding to the diseased part reference region using the dictionary data registered by said registration unit; and
      a determining unit configured to determine whether a second diseased part region is included in the second image based on whether the corresponding region detected by said detection unit is included in the second image.

2. The apparatus according to claim 1, wherein said CPU and memory are further programmed to operate as an image sensing unit configured to perform image sensing in a case in which the determining unit determines that the second diseased part region is included in the second image.

3. The apparatus according to claim 2, wherein said CPU and memory are further programmed to operate as a notification unit configured to provide notification of an instruction to change an image-sensed composition at the time of image sensing by said image sensing unit based on the second diseased part region in a case in which the determining unit determines the second diseased part region is included in the second image.

4. A method of controlling an image processing apparatus, comprising:
   a designation acceptance step of accepting designation of a first diseased part region from a first image of an object to be examined by a medical doctor;
   a determination step of determining a diseased part reference region, of the object to be examined by a medical doctor, surrounding the diseased part region accepted in said designation acceptance step;
   a feature amount extraction step of extracting a feature amount in the diseased part reference region, of the object to be examined by a medical doctor, determined in said determination step;

a registration step of registering the feature amount in the diseased part reference region extracted in said feature amount extraction step into dictionary data;

a detection step of detecting from a second image a corresponding region corresponding to the diseased part reference region using the dictionary data registered in said registration step; and a determining step of determining whether a second diseased part region is included in the second image based on whether the corresponding region detected in said detection step is included in the second image.

5. A non-transitory computer-readable storage medium storing a computer program for causing a computer to execute each step in a method of controlling an image processing apparatus, the method comprising:

a designation acceptance step of accepting designation of a first diseased part region from a first image of an object to be examined by a medical doctor;

a determination step of determining a first diseased part reference region, of the object to be examined by a medical doctor, surrounding the diseased part region accepted in said designation acceptance step;

a feature amount extraction step of extracting a feature amount in the diseased part reference region, of the object to be examined by a medical doctor, determined in said determination step;

a registration step of registering the feature amount in the diseased part reference region extracted in said feature amount extraction step into dictionary data;

a detection step of detecting from a second image a corresponding region corresponding to the diseased part reference region using the dictionary data registered in said registration step; and a determining step of determining whether a second diseased part region is included in the second image based on whether the corresponding region detected in said detection step is included in the second image.

6. The apparatus according to claim 1, wherein said detection unit detects, using the second image obtained by an image sensing unit, the corresponding region corresponding to the diseased part reference region, wherein said determining unit determines whether or not the corresponding region is included in the second image, and wherein said CPU and memory are further programmed to operate as an image sensing processing unit configured to perform image sensing in a case where the corresponding region is included in the second image.

7. The apparatus according to claim 2, wherein the image processing apparatus has a dictionary registration mode of operation, for performing a registration to dictionary data, and an image sensing mode of operation, for obtaining an output image by detecting and image-sensing a diseased part, and wherein said CPU and memory are further programmed to operate as a selection unit configured to select the dictionary registration mode or the image sensing mode.

8. The apparatus according to claim 1, wherein said determining unit determines the second diseased part region is included in the second image in a case in which all of the corresponding region detected by said detection unit is included in the second image.

9. The apparatus according to claim 2, wherein said determining unit determines the second diseased part region is included in the second image in a case in which all of the corresponding region detected by said detection unit is included in the second image.

* * * * *